United States Patent [19]

Powers et al.

[11] Patent Number: 5,675,061
[45] Date of Patent: Oct. 7, 1997

[54] ISOLATION AND CHARACTERIZATION OF AN ACTIN GENE FROM ABALONE

[75] Inventors: Dennis Alpha Powers, Pacific Grove, Calif.; Lynna Madsen Hereford, deceased, late of Port Angeles, Wash., by Anne Madsen, legal representative; Marta Gomez-Chiarri, Pacific Grove, Calif.

[73] Assignee: The Board of Trustees of the Leland Stanford Junior University, Stanford, Calif.

[21] Appl. No.: 286,872

[22] Filed: Aug. 5, 1994

Related U.S. Application Data

[63] Continuation-in-part of Ser. No. 192,272, Feb. 4, 1994, abandoned.

[51] Int. Cl.$^6$ .............................. C12N 5/00; C12N 15/00
[52] U.S. Cl. .................... 800/2; 800/DIG. 1; 435/172.1; 435/172.3; 435/173.6; 435/320.1; 536/23.1; 536/23.5; 536/24.1; 119/234; 935/27; 935/55; 935/63
[58] Field of Search .................. 435/172.1, 172.3, 435/320.1, 69.1, 173.6; 800/2, DIG. 1; 536/23.1, 23.5, 24.1; 119/234; 935/27, 55, 63

[56] References Cited

U.S. PATENT DOCUMENTS 4,834,024  5/1989  Allen et al. ............................ 119/236

OTHER PUBLICATIONS

DE Morse et al (1979) Science 204: 407–410.
RA Firtel (1981) Cell 24: 6–7.
JA Loudon et al (1993) Clinical and Experimental Pharmacology and Physiology 20: 283–288.

M. Krause et al (1989) J. Molecular Biology 208: 381–392.

Frohman, M.A., "RACE: Rapid Amplification of cDNA Ends," *PCR: Protocols: A Guide to Methods and Applications*: 28–32 (1990).

Sigma Chemical Company catalog, "Biochemicals Organic Compounds for Research and Diagnostic Reagents," pp. 112, 486, 1488 & 1490 (1989).

Sun, Z., et al., "A preliminary study on the growth of triploid abalone (Haliotis discus hannai Ino)," Abstract from *Trans. Oceanol. Limnol. Haiyang Huzhao Tongbao* 4: 70–75 (1992).

Vacquier, V.D., et al., "Species–specific sequences of abalone lysin, the sperm protein that creates a hole in the egg envelope," *Proc. Natl. Acad. Sci. USA* 87: 5792–5796 (1990).

Wang, Z., et al., "Triploidization of the Pacific abalone with cytochalasin B and temperature shock," Abstract from *J. Dalian Fish. Coll. Dalian Shuichan Xueyuan Xuebao* 5(1): 1–8 (1990).

Primary Examiner—Bruce R. Campbell
Attorney, Agent, or Firm—Charles K. Sholtz; Gary R. Fabian; Peter J. Dehlinger

[57] ABSTRACT

The present invention describes vectors and methods useful for the production of transgenic mollusks, in particular, transgenic abalone. The invention further describes transgenic mollusks having enhanced growth properties. In addition, the isolation and characterization of an abalone actin gene promoter region is disclosed.

24 Claims, 10 Drawing Sheets

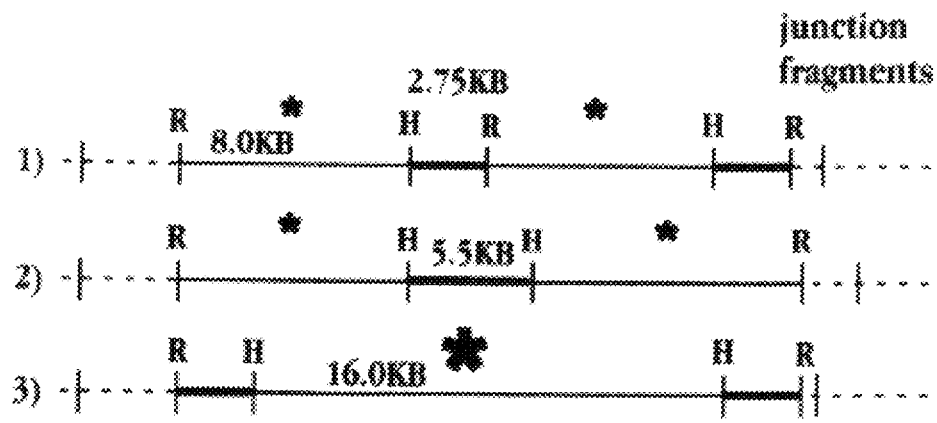
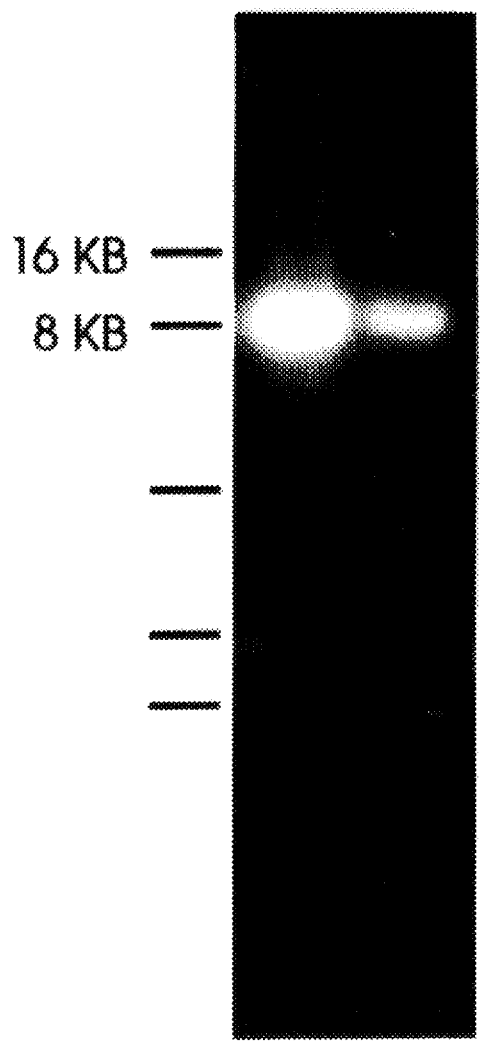
Fig. 3A
Fig. 3B

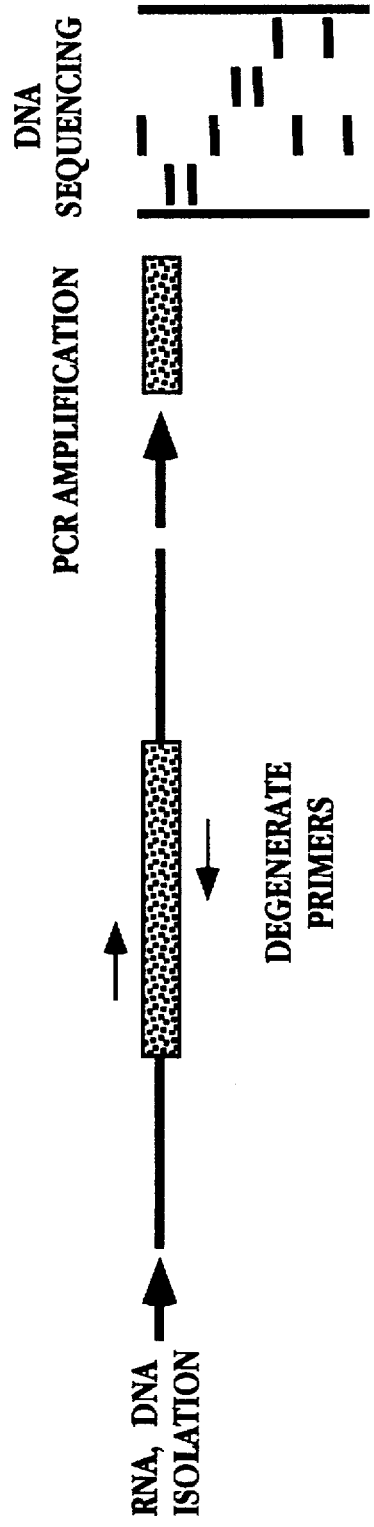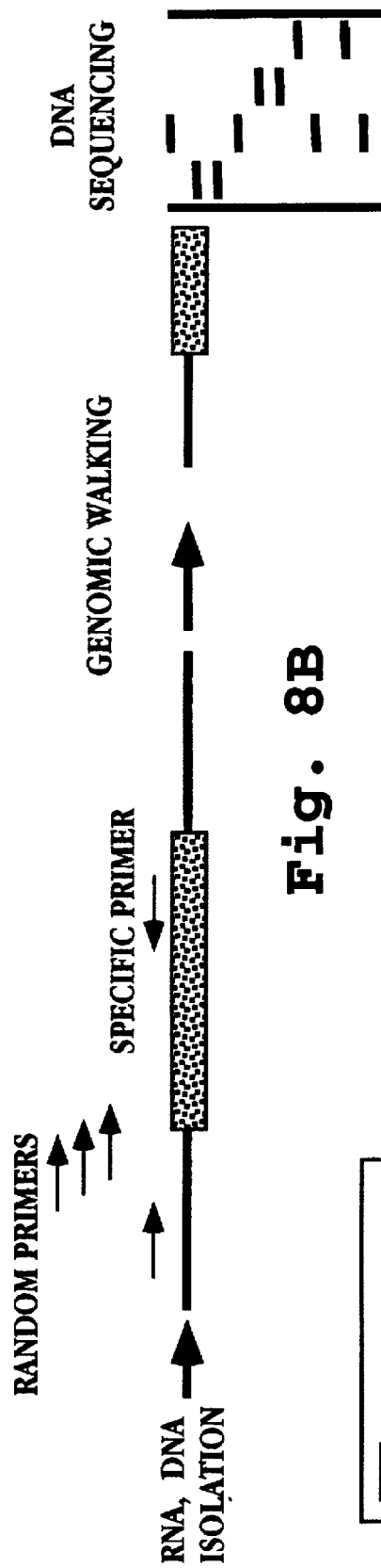

|  | 10 | 20 | 30 | 40 | 50 |  |
|---|---|---|---|---|---|---|
|  | 1234567890 | 1234567890 | 1234567890 | 1234567890 | 1234567890 |  |
|  | GGAACAGTGT | CAAACATATA | TACAAGCTTG | ATGGTGAGAA | ATATTAGCAT | 50 |
|  | TAATACTGTC | ACTTGTTGTT | TAGCATATTA | TTTCTGATAT | ATAAATACTT | 100 |
|  | AGGAAATTCT | ATTTTTCTCA | TGCAAAAAGC | CACTTAACTT | CATCAATAAA | 150 |
|  | ATCGTTATCT | GCACCTAAGA | ATGATCTTCC | ATCATCTCTA | TGTTGACATA | 200 |
|  | CGTTTTATCA | TCCAGATTAT | CAATGAAAGT | CGAAAGATT | ACAACTCCCT | 250 |
|  | CTGAAATATG | AATATTCACA | GTTAGAGGG | CAAGTAAAGC | CAACACAACT | 300 |
|  | ACTTTGCACG | GCGAGAACAA | GCAATATCAG | GGTGTTACAT | TCTGTACATT | 350 |
|  | CGTTAGATAT | TTTACTTCTG | GGTCCAATCC | TTATTACACA | CTGCATTTCT | 400 |
|  | TCCAGGAAGT | TTGGATATAA | CTTTACAATG | CTTTATAACT | GATGAGTAGT | 450 |
|  | AAGCGTTGTA | TGGATTTTAG | AATCTATGCA | TTTCCCAATA | ATGCTGATAT | 500 |
|  | ATTCATTTAA | CTTAATTTAT | TACCAGCATC | ACATTCTTGC | ATTCATGCTC | 550 |
|  | GTCAGCTCGA | GAAGCGCTTC | CCCATTCTCC | GCGCACCATA | CCACGTGGCG | 600 |
|  | TTGTCCTTGC | TTCGGAACG | GGGGTAGGG | GTACTTACTT | CTAGGGAAA | 650 |
|  | GAGAGATCAG | TGCAGATCAC | CCCCGACTGT | GACACATTCT | TCCACATGTA | 700 |
|  | CACATGAAAG | GTTGTTATGC | AATATAATAC | ATTAGAAGGG | TATATTTATT | 750 |
|  | ACAATTACAA | TGGTTACGTT | TCTATTATTC | TCAAACACAA | TCTGATTGGT | 800 |
|  | CGCCTACTAA | TGGGGTATGT | ATAAAAGACG | CCTGGGTCAG | AACATCGATA | 850 |
|  | TTGCATCCGC | TTTCAGTCTT | CAGCTGACAC | ATCGTCTTTC | CCGTTTCTCA | 900 |
|  | CACAGCAACC | TACAACCATG | GATGATGATG | TTGCTGCATT | GGTCTGTGAC | 950 |
|  | AACGGCTCCG | GCATGTGCAA | GGCCGGTTTT | GCCGGTGACG | ACGCTCCCAG | 1000 |
|  | AGCTGTCTTC | CCCTCCATCG | TCGGCCGTCC | TAGACATCAG | GTAACACCGT | 1050 |
|  | TTATTGTCAC | CATGGTAACA | TAGACGTTCA | AGACCTGAAA | TATTTAGTTT | 1100 |
|  | CGCCTACATT | TGTCTCTGT | AGAATACACG | ACGTCGTACA | TAATGACAAA | 1150 |
|  | TGATTTCTTG | TTTCAGGGTG | TGATGGTTGG | TATGGGTCAG | AAAGACAGCT | 1200 |
|  | ACGTCGGTGA | CGAGGCTCAG | TCCAAGAGAG | GTATCCTCAC | TCTCAAGTAT | 1250 |
|  | CCCATCGAGC | ACGGTATCGC | CACCAACTGG | GACGACATGG | AGAAGATCCG | 1300 |
|  | GCATCACACC | TTCTACAACG | AACTCCGAGT | GGCTCCAGAG | GAGCACCYTG | 1350 |
|  | TCCTYCTGAC | AGAGGCTCCC | CTCAACCCCA | AGGCCAACCG | TGAAAGATG | 1400 |
|  | ACCCAGATCA | TGTTCGAGAC | CTTCAACTCT | CCAGCTATGT | GTGTGGCCAT | 1450 |
|  | CCAGGCTGTT | CTGTCTCTGT | ACGCTTCTGG | TCGTACCACG | GGTATTGTTC | 1500 |
|  | TGGACTCTGG | TGATGGTGTT | ACCCACACTG | TTCCCATCTA |  | 1540 |

Fig. 9

ISOLATION AND CHARACTERIZATION OF AN ACTIN GENE FROM ABALONE

This application is a continuation-in-part of co-owned, U.S. patent application Ser. No. 08/192,272, filed 4 Feb. 1994, abandoned, herein incorporated by reference.

FIELD OF THE INVENTION

The present invention relates to transgenic mollusks, in particular shellfish, and further to methods of genetic engineering of mollusks, including abalone. Further, the invention relates to the isolation and characterization of abalone actin gene sequences, and uses thereof.

REFERENCES

Agellon, L. B., et al., *Can. J. Fish. Aquat. Sci.* 45:146–151 (1988).

Ausubel, F. M., et al., *Current Protocols in Molecular Biology*, John Wiley and Sons, Inc., Media Pa.

Bellen, H. J., et al., *Genes Dev.* 3:1288–1300 (1989).

Chong, S. S. C., and Vielkind, J. R., *Theor. Appl. Genet.* 78:369–380 (1989).

Crea, R., U.S. Pat. No. 4,888,286, issued Dec. 19, 1989.

Davies, J. A., et al., *J. Mol. Biol.* 189(1):13–24 (1986).

de Wet, J. R., et al., *Mol. Cell. Biol.* 7:725–737 (1987).

Du, S. J., et al., *Bio/Technology* 10:176–181 (1992).

Eaton, M. A. W., et al., U.S. Pat. No. 4,719,180, issued Jan. 12, 1988.

Ebert, E. E., "Abalone Aquaculture: A North America Regional Review" in *Abalone of the World; Biology, Fisheries and Culture* (Shepherd, S. A., et al., eds.) Blackwell Scientific Publications Ltd., Oxford, England, pp. 570–180 (1992).

Frohman, M. A., et al., *Proc. Natl. Acad. Sci. USA* 85:8998–9002 (1988).

Frohman, M. A., in *PCR Protocol: A Guide to Methods and Applications*, p.28, Academic Press (1990).

Fryberg, E. A., et al., *Cell* 33:115–123 (1983).

Gibbs, P. D. L., et al., *2nd Int. Marine Biotech. Conf. (IMBC)* Baltimore, Md., Abstracts, p. 79 (1991).

Gonzalez-Villansenor, L. I., et al., *Gene* 65, pp. 239–246.

Gorman, C. M., et al., *Mol. Cell. Biol.*, 2:1044 (1982).

Gutzman del Proo, A., "A Review of Abalone and its Fishery in Mexico" in *Abalone of the World; Biology, Fisheries and Culture* (Shepherd, S. A., et al., eds.) Blackwell Scientific Publications Ltd., Oxford, England, pp. 438–447 (1992).

Guyomard, R. D., et al., *Biochimie* 71:85–863 (1989).

Hackett, P. B., "The Molecular Biology of Transgenic Fish" in *Molecular Biology of Fishers, Vol. 2* (Hochachka, P., and Mommsen, T., eds.) in press (1993).

Hahn, K. O., in *Handbook of Culture of Abalone and Other Marine Gastropods* (Hahn, ed.) CRC Press, Inc., Boca Raton, Fla., pp. 71–98 (1989).

Hammer, R. E., et al., *Nature* 315:680–683 (1985).

Harvey, D., *USDA Aqua-5* pp. 19 (1990).

Henikoff, S., *Methods Enzymol.* 155:156–165 (1987).

Hitzeman, R. A., et al., U.S. Pat. No. 4,775,622, issued Oct. 4, 1988.

Hoheisel, J., and Pohl, F. M., *Nucl. Acids Res.* 14:3605 (1986).

Irvine, et al., *Development* 111:407–424 (1991).

Joosse, J., and Garaerts, W. P. M., "Endocrinology" in *The Mollusca, Vol. 4, Physiology, Part 1* (Saleuddin, A. S. M., and Wilber, K. M., eds.) Academic Press, London, England, pp. 317–406 (1983).

Kawasaki, E. S., et al., in *PCR Technology: Principles and Applications of DNA Amplification* (H. A. Erlich, ed.) Stockton Press (1989).

Koelle, M., et al., *Cell* 67:59–77 (1991).

Koelle, Michael, "Molecular Analysis of the *Drosophila Melanogaster* Ecdysone Receptor Complex," Ph.D. thesis, Stanford University 1992.

Liu, Z. B., et al., *Mol. Cell. Biol.* 10:3432–3440 (1990a).

Liu, Z. B., et al., *Bio/Technology* 8:1268–1272 (1990b).

Liu, Z. B., et al., *DNA Sequence* 1:125–136 (1990c).

Maniatis, T., et al., *Molecular Cloning: A Laboratory Manual*, Cold Spring Harbor Laboratory (1982).

Moav, B., et al., in "Expression of Heterologous Genes in Transgenic Fish" in *Transgenic Fish* (Hew, C. L., ed.) World Scientific Publishing Co., Singapore, pp. 120–141 (1992a).

Moav, B., et al., *Mol. Mar. Bio. Biotech.* 1:338–345 (1992b).

Moriyama, S. S., et al., *Xth Internal Symp. on Comp. Endocrin.* Abstracts, Malaga, Spain, pp. 243 (1989).

Moriyama, Ph.D. Thesis, University of Kitsato (in Japanese) 1992.

Morse, E. D., *Biennial Rpt., U. of California Sea Grant Program*, pp. 83–87 (1981).

Morse, E. D., *Aquaculture* 39:263–282 (1984).

Oeda, K., et al., U.S. Pat. No. 4,766,068, issued Aug. 23, 1988.

Paynter, K. T., and Chen, T. T., *Biol. Bull.* 181:459–462 (1991).

Prince, J. D., and Shepherd, "Australian Abalone Fisheries and Their Management" in *Abalone of the World; Biology, Fisheries and Culture* (Shepherd, S. A., et al., eds.) Blackwell Scientific Publications Ltd., Oxford, England, pp. 407–426 (1992).

Rio, R. C., et al., *Mol. Cell. Biol.* 5(8):1833 (1985).

Rokkones, E. P., et al., *J. Comp. Physiol. B.* 158:751–758 (1989).

Rutter, W. J., et al., U.S. Pat. No. 4,769,238, issued Sep. 6, 1988.

Sambrook, J., et al., *Molecular Cloning: A Laboratory Manual*, Cold Spring Harbor Laboratory Press, New York. N.Y. (1989).

Sara, V. R., and Hall, K., *Physiological Rev.* 70:591–614 (1990).

Schweinfest, C. W., et al., *Gene* 71(1):207 (1988).

Sekine, S., et al., *Proc. Natl. Acad. Sci. USA* 82:4306–4310 (1985).

Stuart, G. W., et al., *Development* 103:403–412 (1988).

Tarr, R. J. K., "The Abalone Fishery of Mexico" in *Abalone of the World; Biology, Fisheries and Culture* (Shepherd, S. A., et al., eds.) Blackwell Scientific Publications Ltd., Oxford, England, pp. 438–447 (1992).

Tegner, M. J., et al., "The California Red Abalone Fishery: A Case Study in Complexity" in *Abalone of the World; Biology, Fisheries and Culture* (Shepherd, S. A., et al., eds.) Blackwell Scientific Publications Ltd., Oxford, England, pp. 370–383 (1992).

Vanderkerckhove, J., and Weber, K., *Proc. Natl. Acad. Sci. USA* 75:1106–1110 (1978a).

Vanderkerckhove, J., and Weber, K., *Eur. J. Biochem.* 90:451–462 (1978b).

Yoshio, T., et al., U.S. Pat. No. 4,849,350, issued Jul. 18, 1989.

Zhang, P., et al., *Mol. Rep. Dev.* 25:3–13 (1990).

Zhu, Z., et al., *Kexue Tongbau* 31:998–405 (1986).

BACKGROUND OF THE INVENTION

The U.S. market for seafood is large and growing with per capita seafood consumption rising 23% in the last decade. During this period, the consumer price index for seafood jumped 244%, while red meat prices rose only half that amount. Despite efforts to manage wild finfish and shellfish populations at a sustained yield level, the U.S. consumes increasingly greater amounts than it produces from its fishers, thus depleting the resource. Ocean harvests worldwide are expected to meet only 90 million metric tons of the projected demand of 114 million metric tons in the year 2000 (Harvey, 1990).

This global picture is mirrored in the California abalone industry. From 1931 until 1968, commercial abalone landings averaged around 900 metric tons a year. Since 1968, landings have decreased to approximately 15% of these levels. This decline has been attributed to a number of factors, the most important of which is probably fishing pressure brought about by demand from the Far East (Tegner, 1989).

Despite intensive efforts by the California Department of Fish and Game to restore the fishery, current landings remain at their 1968 levels. The decline in the California abalone fishery is paralleled by similar declines in Mexico (Gutzman del Proo, 1992), South Africa (Tarr, 1992), and Australia (Prince and Shepherd, 1992).

As the supply of abalone diminishes, their per limit value continues to increase. Between 1973 and 1988, the price paid to divers has increased 800%, over twice the rate of inflation (Tegner, et al., 1992). This increased demand has led to the development of techniques for commercial cultivation. These efforts have been concentrated mainly in Japan and California, although California is unique in the development of seawater systems for intensive cultivation on land (Ebert, 1992).

SUMMARY OF THE INVENTION

In one aspect the present invention includes a transgenic mollusk containing a DNA sequence heterologous to the mollusk. The heterologous DNA sequence may be integrated or extrachromosomal. In one embodiment the DNA sequence is flanked by regulatory sequences, which are effective to allow expression of the DNA sequence in the mollusk (e.g., expression of an RNA or protein). These regulatory sequences can be derived from a mollusk, such as abalone, or from other sources, including *Drosophila melanogaster* genes. Embodiments of the invention include use of actin gene regulatory sequences from either *Drosophila melanogaster* or abalone. A preferred embodiment utilizes the actin gene promoter described herein.

In one embodiment of the invention, the regulatory sequences are derived from the *Drosophila melanogaster* ACT-5 promoter and the heterologous DNA sequence encodes coho salmon growth hormone. When this construct is used to generate transgenic abalone, growth of the abalone is enhanced.

Heterologous DNA sequences useful in the practice of the present invention include DNA sequences that encode products that promote growth enhancement (e.g., a growth hormone or insulin-like growth factor). Further included are other DNA sequences encoding products affecting the taste or texture of mollusk tissue.

The present invention also includes expression vectors useful for making transgenic mollusks by the method of the present invention. Expression vectors typically include (i) a first DNA sequence flanked by regulatory elements effective to allow expression of the sequence in a mollusk, wherein the regulatory elements are derived from a mollusk gene, and (ii) second DNA sequences allowing the propagation of the vector in a secondary host. Exemplary second sequences include DNA sequences having an origin of replication and a selectable marker, which are both functional in the secondary host. Secondary hosts include bacteria, yeast and insect cells. The expression vectors can carry the regulatory elements and DNA coding sequences discussed above.

In another embodiment, the present invention includes an expression vector containing an abalone actin gene promoter region adjacent a cloning site useful to facilitate the insertion of any coding sequence of interest.

The present invention also includes a method for transfecting a mollusk. In the method, a vector is provided which contains DNA sequences of interest. The vector is introduced into a selected mollusk, for example, by electroporation. Transfected mollusks, that is, mollusks now bearing the DNA of interest, are identified based on the presence of the DNA sequence, for example, by hybridization analysis or by manifestation of a characteristic associated with the DNA sequence (e.g., presence of a reporter gene).

The DNA sequence can encode a gene that promotes growth enhancement, such as, a growth factor or an insulin-like growth factor.

The introduced DNA may be integrated or extra-chromosomal. In one embodiment, introduction of the DNA is accomplished by electroporating the vector into a fertilized mollusk egg, for example, a fertilized abalone egg. Typically, the DNA sequence is flanked by regulatory sequences which are effective to allow expression of the DNA sequence in the transgenic mollusk.

Another embodiment of the present invention includes a method for the recombinant expression of a protein in a mollusk. The method includes using a transgenic mollusk carrying a heterologous DNA sequence encoding a protein grown under conditions permissive for the expression of the protein.

The invention further includes a method for enhancing the growth of a mollusk, where a transgenic mollusk is generated that carries a heterologous DNA sequence encoding a gene that promotes growth enhancement (e.g., a growth hormone or insulin-like growth factor). The transgenic mollusk is then cultured under conditions permissive for the growth enhancing protein.

The present invention also includes a duplex DNA fragment containing a DNA sequence encoding a polypeptide, and adjacent the DNA sequence, a promoter effective to promote transcription of the polypeptide, where the promoter is an abalone actin gene promoter and the DNA sequence is not the abalone actin gene. In this embodiment, the polypeptide coding sequences are heterologous to the promoter sequences. In one embodiment, the DNA sequence is a gene that promotes growth enhancement, such as, a growth hormone (e.g., coho salmon growth hormone) or insulin-like growth factor.

Such duplex DNA fragments are useful, for example, as expression cassettes for insertion into any vector of interest.

These and other objects and features of the invention will be more fully appreciated when the following detailed description of the invention is read in conjunction with the accompanying drawings.

BRIEF DESCRIPTION OF THE FIGURES

FIG. 3A shows a partial restriction map of potential junction fragments. FIG. 3B shows DNA hybridization data for transgenic abalone.

FIGS. 8A and 8B schematically represent the steps involved in the isolation of the abalone actin promoter.

FIG. 9 presents the sequence (SEQ ID NO:5) of the abalone actin promoter and adjacent regions.

DETAILED DESCRIPTION OF THE INVENTION

I. DEFINITIONS

Figure 1:
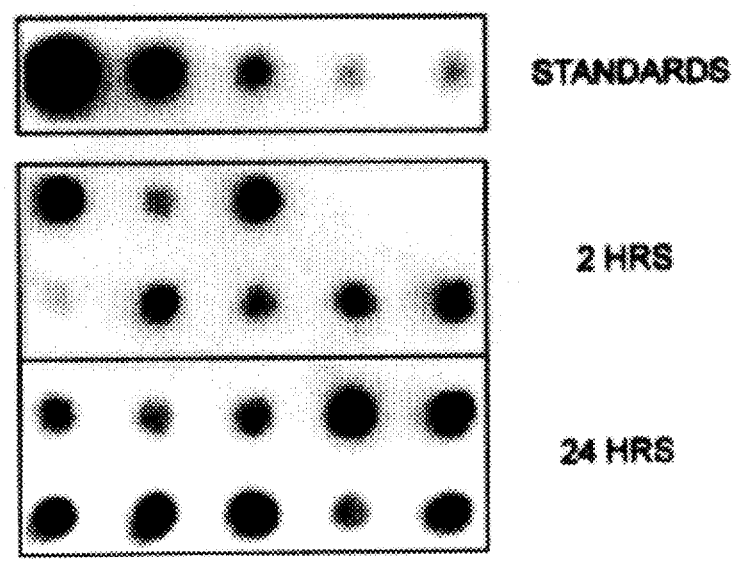
FIG. 1 demonstrates uptake and retention of plasmid DNA into electroporated abalone eggs.

Homologous DNA refers to DNA not introduced into a host organism by recombinant means.

Heterologous DNA refers to DNA which has been transfected into a host organism. Typically, heterologous DNA refers to DNA that is not originally derived from the transfected or transformed cells' genomic DNA (e.g., CAT and β-galactosidase gene sequences). However, any DNA introduced into an organism by recombinant means is referred to as heterologous DNA (e.g., introduction into an abalone of an expression vector carrying abalone growth hormone gene).

Extra-chromosomal DNA refers to plasmid DNA introduced into a host cell, where the plasmid DNA has not integrated into the genomic DNA of the host cell.

The term "mollusk" herein refers to members of the phylum Mollusca, including, the classes Bivalvia (e.g., oysters), Gastropoda (e.g., abalone), and Cephalopoda (e.g., squid).

II. DEVELOPMENT OF VECTORS USEFUL FOR THE GENERATION OF TRANSGENIC SHELLFISH

A. Introduction of Exogenous DNA

The development of an effective method for production of transgenic mollusks needs to take into account certain peculiarities of the organisms. An exemplary mollusk, for the purposes of the present invention, is abalone.

Abalone belong to a loose group of marine invertebrates known as "broadcast spawners." In such organisms, fertilization is external and is preceded by the release of large numbers of sperm and eggs from gravid adults. A large adult female (7 inches) will produce on the order of 10 million eggs and, under hatchery conditions, fertilization rates greater than 95% are achieved.

Development proceeds rapidly and synchronously: Meiosis I (appearance of the first polar body) is complete by 20 minutes; Meiosis II (appearance of the second polar body) is complete by 30 minutes, and the first cleavage is complete by 2 hours. By 24 hours, gastrulation is completed and a velum, a simple locomotory system for swimming, has developed.

At this point, the egg hatches, releasing a veliger larva. During the next 24 hours, the primary differentiation of virtually all adult tissue occurs, resulting in what is termed a trochophore larva. Trochophore development continues for five to seven days, at which time settlement occurs.

Settlement involves attachment of the animal to a solid substrate, after which it loses its swimming apparatus, develops an adult shell, and begins grazing. For reasons which are not well understood, settlement results in large mortalities—under hatchery conditions, only two to five percent of competent veliger larvae successfully settle. While this is not a major hindrance to hatcheries, due to the high fecundity of the organism, it does impose problems for development of an efficient transgenic technology.

To improve the chances for integration of exogenous DNA into the germline, the DNA is introduced prior to the first mitotic cleavage. Introducing DNA by electroporation allows treatment of a large number of eggs within relatively short time frame of the first mitotic cleavage (approximately two hours). Although introduction of DNA by electroporation is a preferred embodiment of the invention, alternative approaches to introducing exogenous DNA may be used as well, such as microinjection.

A further consideration when dealing with the transfection of abalone is its position in the animal kingdom and the influence of this position upon the choice of suitable promoters for use in expression vectors. "Classic" vertebrate expression vectors usually employ promoters which are expressed at high levels in a number of tissues. Most popular among these ar the promoters derived from the long terminal repeats (LTRs) of the retroviruses cytomegalovirus (CMV) and Rous sarcoma virus (RSV).

However, because of the evolutionary distances separating vertebrates and mollusks, vertebrate promoters are not likely to effect expression in molluscan tissue. Experiments performed in support of the present invention have utilized *D. melanogaster* promoters (e.g., ACT5-C; Koelle, 1993), an organism more closely related to mollusks than vertebrates. Other *D. melanogaster* promoters/expression vectors may also be useful in the practice of the present invention (e.g., Rio, et al., 1985; Davies, et al., 1986; Schweinfest, et al., 1988).

Exemplary plasmid pMK18 is described in Example 1. Plasmid pMK18 contains the ACT5-C promoter, a β-actin promoter. This promoter was chosen because the gene is expressed throughout development, as well as in most adult tissues (Fryberg, et al., 1983). The plasmid contains an "expression cassette" consisting of the *E. coli* β-galactosidase gene and the 5' untranslated region of the ubx gene.

Experiments performed in support of the present invention utilized plasmid pMK18 for transfection of fertilized abalone eggs by electroporation. Initial optimization of electroporation conditions was accomplished using dot blot hybridization to detect introduction of exogenous DNA into the fertilized eggs (Example 2). DNA was extracted from single eggs or larvae, which was then fixed to nitrocellulose and hybridized with the appropriate radiolabelled plasmid DNA.

Dot blots were performed at two time points: (i) at the two-to-four cell stage—to monitor DNA uptake, and (ii) immediately after hatching—to monitor DNA retention. A typical dot blot after optimization of electroporation conditions is shown in FIG. 1 (Example 3). In the figure it can be seen that DNA is taken up and retained in approximately 80–100% of all electroporated eggs.

Figure 4:
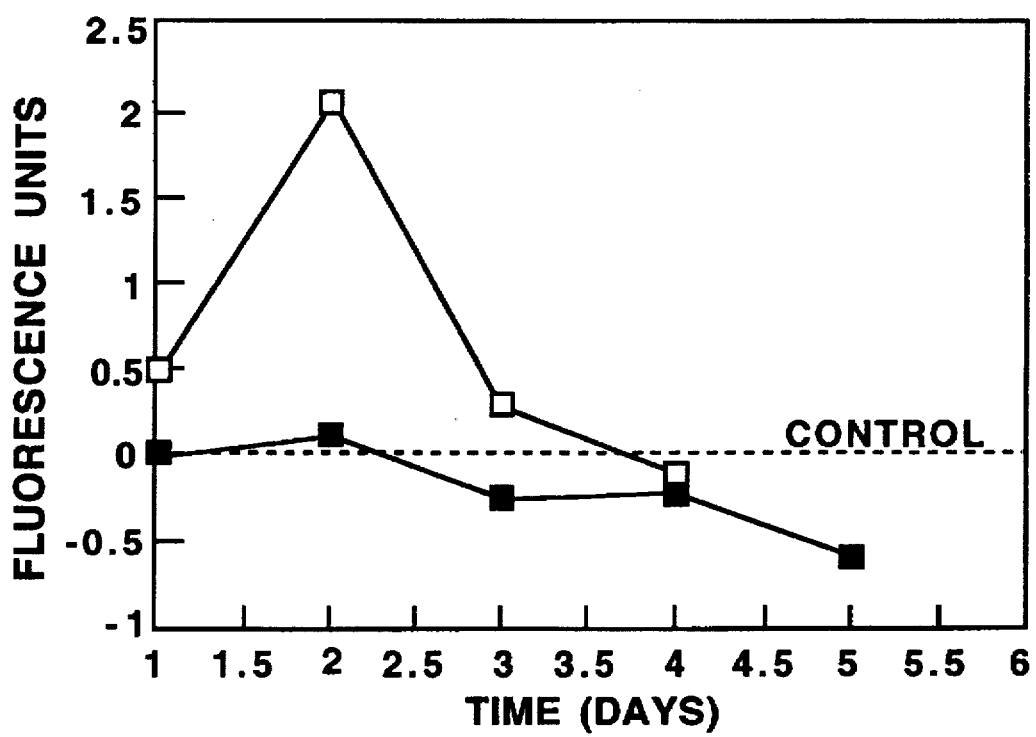
FIG. 4 represents expression of β-galactosidase in electroporated larvae.

To test for expression of the exogenous DNA in the transgenic abalone, pools of fifty larvae were collected at various times during the period of larval development and assayed for β-galactosidase activity (Example 4). The results of these assays are shown in FIG. 4. The data demonstrate that β-galactosidase is expressed when pMK18 (β-actin promoter) is employed.

Activity is observed in trochophore larvae (day one), and this activity reaches a maximum in veliger larvae (day two). The decline in enzyme activity is not due to loss of plasmid sequences, since dot blots reveal the retention of plasmid DNA throughout the larval period. The peak of β-galactosidase activity apparently occurs between the transition from trochophore to veliger—a point of maximal cell division. Since β-actin levels are positively correlated with cell division, it may be that the Drosophila actin promoter is acting in a developmentally correct manner.

The data also demonstrate that the vertebrate retroviral promoter CMV does not seem to be active. Similar results were obtained with the RSV promoter.

Figure 2:
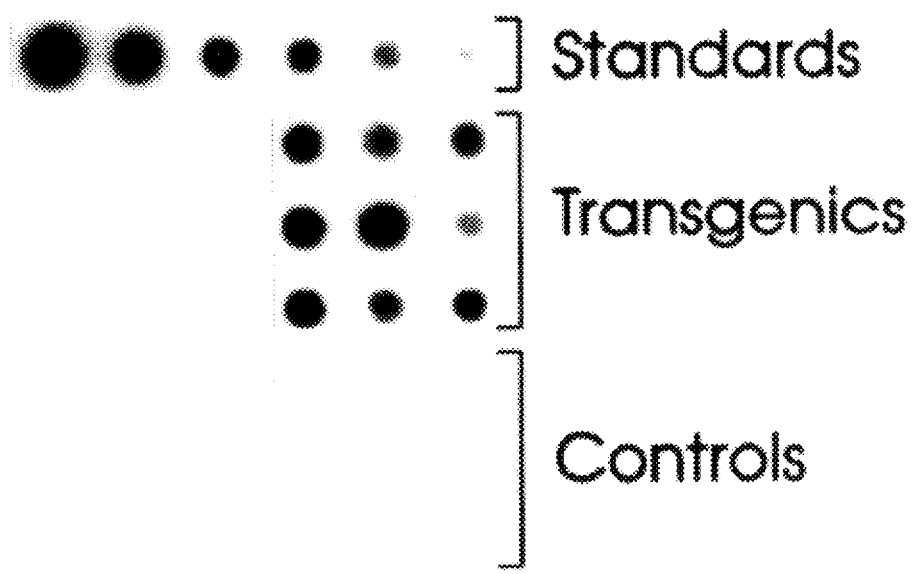
FIG. 2 shows retention of electroporated DNA in three-month-old juvenile abalone.

To test whether plasmid DNA was retained and expressed post-settlement, approximately 6,000 eggs were electroporated using pMK18 DNA from which we subsequently obtained approximately 200 juveniles. The juveniles were sampled at three, six, and nine months of age (Example 3). A typical dot blot from three-months-old juveniles is shown in FIG. 2.

Of the nine animals tested, all retained DNA and, of these, six showed significant levels of β-galactosidase expression (Table 1; assayed essentially as described in Example 4).

TABLE 1

| B-GALACTOSIDE ACTIVITY IN CONTROL AND EXPERIMENTAL JUVENILE ABALONE | |
| --- | --- |
| SAMPLE | β-GALACTOSIDASE ACTIVITY* |
| control 1 | 6.2 |
| control 2 | 6.8 |
| control 3 | 7.4 |
| control 4 | 7.0 |
| control 5 | 6.5 |
| control 6 | 6.0 |
| control 7 | 6.3 |
| control 8 | 6.7 |
| control 9 | 7.3 |
| control 10 | 8.0 |
| transgenic 1 | 19.2 |
| transgenic 2 | 12.0 |
| transgenic 3 | 25.0 |
| transgenic 4 | 12.6 |

TABLE 1-continued

| B-GALACTOSIDE ACTIVITY IN CONTROL AND EXPERIMENTAL JUVENILE ABALONE | |
| --- | --- |
| SAMPLE | β-GALACTOSIDASE ACTIVITY* |
| transgenic 5 | 14.5 |
| transgenic 6 | 7.8 |
| transgenic 7 | 12.8 |
| transgenic 8 | 8.4 |
| transgenic 9 | 14.0 |
| transgenic 10 | 16.0 |

*β-galactosidase activity is defined as fluorescence at 450 nm/20 min/mg DNA. The activity is the average of two determinations with an error of 1 to 2%.

Similar results were obtained from six- and nine-months old juvenile abalone. Although plasmid DNA persists in juveniles, it must be integrated into genomic DNA for stable transgenic lines to be established. DNA hybridization analysis of uncut genomic DNA revealed that the plasmid sequences were high molecular weight DNA. Such high molecular weight could be due to concatenation, or to concatenation and integration.

To distinguish between these possibilities, genomic DNA was cut with HindIII which cuts asymmetrically in the EcoRI linearized plasmid used for electroporation (Example 3, FIG. 3A). The DNA was analyzed by hybridization with a 200 bp fragment of pMK18 (FIG. 3A).

The results of the hybridization analysis were as follows. A strong 8 kb signal, corresponding to two of the three possible types of concatenates, was observed in all genomic DNA samples. A faint approximately 16 kb signal, corresponding to the third type of concatenate, was observed in some of the blots. These results suggest that most of the concatenates may be head-to-tail multimers, as has been observed in fish (Stuart, et al., 1988; Chong and Vielkind, 1989).

Junction fragments were observed approximately 70% of the time, suggesting an extremely high degree of integration. An autoradiogram showing both integrated and un-integrated DNA is shown in FIG. 3B (Example 3).

Although the ACT5-C promoter functions in both larvae and juvenile abalone, it appears to do so at only about 5 to 10% efficiency relative to its expression in Drosophila S2 cells. Development of more efficient mollusk expression vectors is described below.

Figure 6:
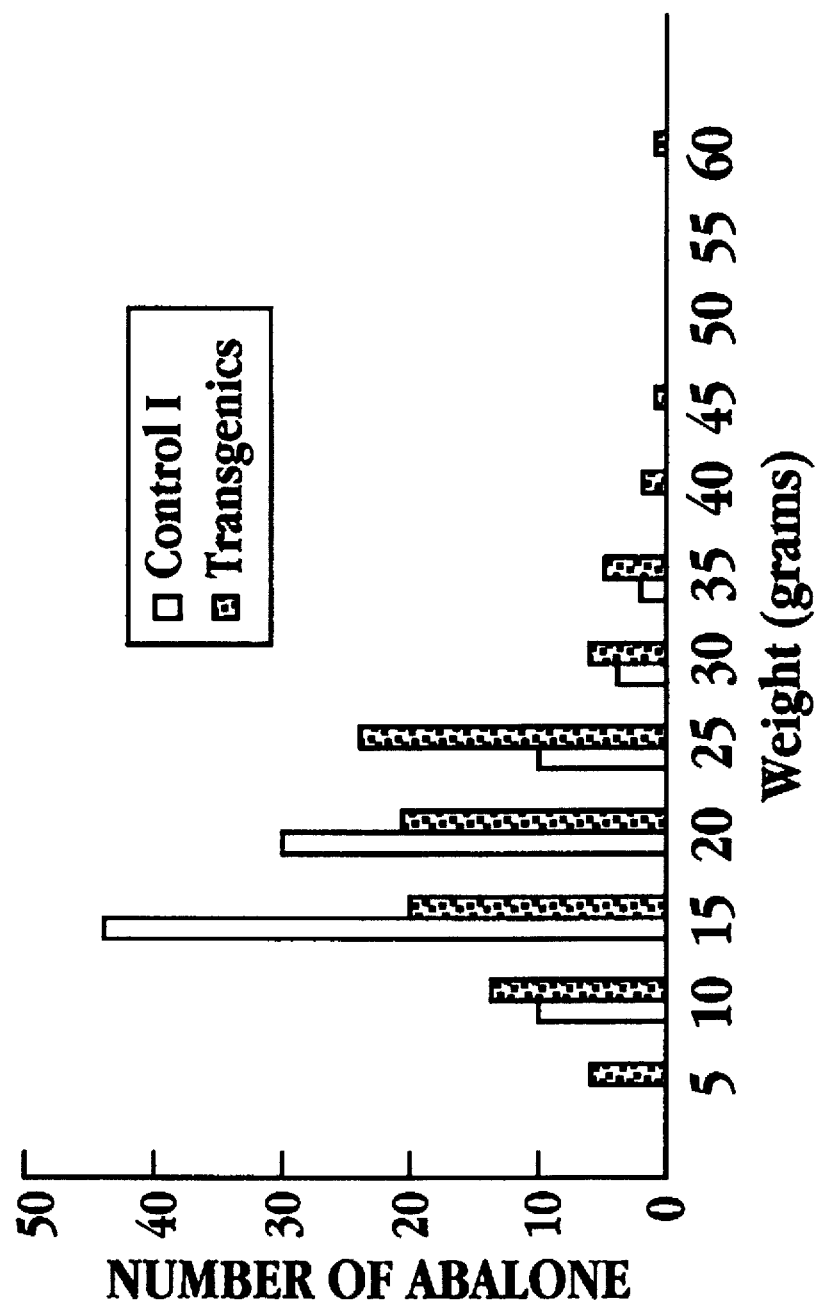
FIG. 6 shows a comparison of weight of abalone transformed with pLH3 with non-transgenic controls.

Transgenic abalone carrying the coho salmon Growth Hormone (csGH) gene (Gonzalez-Villansenor, et al.) under the regulation of the ACT5-C promoter have also been constructed. The sequence of the csGH gene is presented as SEQ ID NO:1. The vector containing the csGH gene under ACT5-C control was designated pLH2. The weight distributions of transgenic abalone, carrying the pLH2 vector, relative to control (wild type) abalone were determined. FIG. 6 shows the result of one such analysis. The data in the figure demonstrate that the transgenic abalone have a wider weight distribution with a higher mean weight than the nontransgenic controls. These results demonstrate the efficacy of generating transgenic mollusks having enhanced growth properties.

The production of gynogens and triploids is described in co-owned, co-pending U.S. application entitled "A METHOD FOR THE ENHANCEMENT OF GROWTH OF ABALONE," filed on even date herewith and herein incorporated by reference. Gynogens permit selfing within one generation and provide a mechanism to rapidly homozygose transgenics, as well as expedite more classical breeding approaches. For example, gynogens are used on the F1 to homozygose transgenes—the F2 are then be made sterile by producing triploids.

Furthermore, triploids (which comprise one component in the production of gynogens) allow production of sterile seed stock, thereby mitigating against environmental concerns over genetically engineered organisms.

III. DEVELOPMENT OF SHELLFISH VECTORS

The present invention also relates to the development of "all abalone" or "all mollusc" expression vectors. Inducible promoters, such as, metallothionein and heat shock promoters (as previously used in fish) can be induced by external stimuli. However, such inducible promoters are not realistically adaptable to large-scale commercial production.

Grow out of abalone occurs in tanks with continuously flowing seawater. It would not be cost-effective nor environmentally prudent to attempt to regulate water temperature or chemical composition on the scale which industrial production demands.

A. Isolation of an Abalone β-Actin Promoter

Experiments performed in support of the present invention are directed to the construction of an abalone expression vectors using the β-actin promoter. This promoter was selected based on two considerations. First, β-actin in expressed in high levels in a number of adult tissues (Fryberg, et al., 1983). Second, it is possible to modulate β-actin promoter activity by constructing vectors with differing combinations of elements responsible for expression (Liu, et al., 1990a; Liu, et al., 1990c). This property is important for expression of some proteins, such as growth hormone where the response of an organism is dependent upon the level of circulating hormone. In the case of growth hormone (GH), organismal growth is proportional to hormone concentration up to a certain optimum, above which it has either no or even slightly inhibitory effects (Agellon, et al., 1988; Moriyama, 1992).

The actin genes are a multigene family (Vanderkerckhove and Weber, 1978a, 1978b). Because the genes are highly conserved, it is not possible to design either probes or primers which distinguish β-actins from α- or γ-actins. In contrast, the 3' untranslated regions do not show extensive homology (Fryberg, et al., 1983; Liu, et al., 1990c) and can be used to identify a specific actin DNA sequence.

To isolate the abalone β-actin gene, a portion of the coding region of the gene was first isolated by polymerase chain reaction amplification (Example 5A). Using a set of degenerate primers for invertebrate actin, an approximately 400 bp fragment within the coding region of the abalone β-actin gene was isolated (Example 5A, FIGS. 5A, 5B and 8A).

From the approximately 400 bp sequence, abalone β-actin sequence specific primers are synthesized. Using these primers, both the three and five prime ends of the gene are isolated using the PCR rapid amplification of cDNA ends (PCR-RACE) reaction (Frohman, 1988, 1990).

After isolation of the 5' and 3' ends, the sequences are determined. Oligonucleotide probes specific to the 5' and 3' untranslated ends of the gene are synthesized. These oligonucleotides are used as hybridization probes against abalone genomic DNA clones carried in lambda-gt10 (Stratagene, La Jolla, Calif.). Positively hybridizing clones are identified and subject to restriction endonuclease cleavage mapping. Cleavage fragments are hybridized with the oligonucleotides to identify appropriately sized restriction fragments containing the actin gene and its promoter, as well as 3' and 5' untranslated regions.

The actin gene-containing restriction fragment is cloned by construction of a size-selected library using standard techniques (Sambrook, et al., 1989). The DNA sequence of the entire actin insert is then determined.

Figure 10:
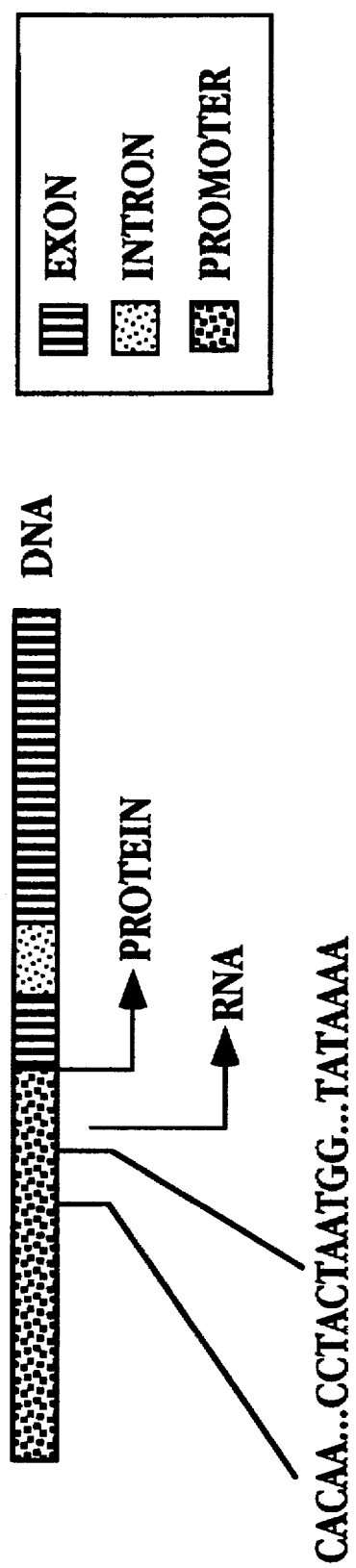
FIG. 10 presents a schematic of the structure of the abalone actin promoter.

Sequences comprising a 5' region of the abalone actin gene, including 5' non-translated sequences have been determined (Example 5B). These sequences are shown in FIG. 9 (SEQ ID NO:5). FIG. 10 presents a schematic representation of the region of the actin gene that has been sequenced. Transient expression assays (Example 5B, Table 2) demonstrate that the actin gene promoter is functional.

The abalone β-actin gene can be used to construct expression vectors (Example 5C). In one embodiment, the abalone actin promoter sequences can be used to construct vectors useful for the transformation of abalone, for example, where a growth hormone gene is placed under its control.

Promoters from other suitable mollusk genes (for example, hexokinase, phosphoglycerate kinase, pyruvate kinase) can be isolated following the procedures essentially as described herein for β-actin.

B. Construction of Expression Vectors

Actin promoter specific motifs are identified by comparison with the other actin promoters. Similar comparisons can be made for other isolated abalone genes. Promoter regions and other 5' and 3' functional regions are identified by deletion mapping (Example 5B). Deletions are sequenced and the end-points, relative to the entire actin gene clone, are determined. Plasmids are constructed containing various proportions of the promoter and the 5' and 3' untranslated regions.

Polylinker sites are typically inserted between 5' and 3' untranslated gene regulatory regions for rapid cloning. Polylinkers usually containing a number of unique restriction enzyme endonuclease sites, e.g., as in the polylinker of pUC18 (Clontech, Palo Alto, Calif.)). Expression vector DNA uptake and DNA integration into fertilized eggs is determined as described in Examples 2 and 3.

Actin gene expression cassettes (i.e., 5'/3' actin sequences flanking a polylinker) are typically cloned into shuttle vectors for ease of manipulation and isolation of large quantities of vector DNA. A number of such shuttle vectors are commercially available (Clontech, Palo Alto, Calif.; Stratagene, La Jolla, Calif.). Shuttle vectors typically contain an origin of replication (for plasmid propagation in a selected host, e.g., the origin of replication can be colE1-type) and a selectable marker gene which allows selection in the host cells (e.g., for bacteria, the β-lactamase gene ($Amp^R$)).

C. Determination of Levels of Expression

Levels of gene expression using the expression vectors of the present invention, are determined by generation of transgenic abalone and characterization of expression of the heterologous DNA in living larvae and juveniles. A number of reporter genes are useful for the quantitation of gene expression, including, β-galactosidase, chloramphenicol acetyl-transferase (CAT), and luciferase (de Wet, et al., 1987; Gibbs, et al., 1991) genes. Typically, the reporter gene is inserted into the expression cassette (e.g., the actin gene expression cassette) as an in-frame fusion.

Levels of gene expression are quantitated by standard enzymatic assays for the detection of the selected reporter gene (e.g., CAT enzyme assay systems, Promega, Madison, Wis.).

Further, quantitation of the levels of expression is performed using RNA hybridization analysis (Ausubel, et al.; Sambrook, et al.) and comparing the levels of the endogenous gene RNA (e.g., β-actin mRNA) to the levels of reporter gene RNA (e.g., luciferase mRNA).

IV. ISOLATION OF SHELLFISH GENES AFFECTING GROWTH

A. Growth Hormone Genes

Insertion of growth hormone (GH) genes has resulted in increased growth rates in a number of commercially important aquatic organisms, such as loach (*Misgurnus anguillicaudatus*) (Zhu, et al., 1986), carp (*Cyprinus carpio*) (Zhang, et al., 1990), Atlantic salmon (*Salmo salar*) (Rokones, et al., 1989; Du, et al., 1992), rainbow trout (*Onorhynchus mydiss*) (Guyomard, et al., 1989), northern pike (*Esox lucius*) and walleye (*Stizostedion vitreum*) (Moav, et al., 1992a). Transgenic fish are typically one to three times larger than their non-transgenic siblings.

Commercially important shellfish—abalone and oysters, respond to exogenous GH (Morse, et al., 1981, 1984). Incubation of abalone larvae at metamorphosis with human GH resulted in approximately a 10% increase in shell length after four days. Recently, Moriyama (1992) has shown that either injection or immersion of juvenile abalone with recombinant salmon hormone results in a two-to-three-fold weight increase.

Similar results have been reported by Paynter and Chen (1991) for the eastern oyster (*Crassostrea virginica*). The positive effects of GH on these shellfish most likely reflect the presence of complex hormonal systems in the primitive mollusks (Joosse and Garaerts, 1983). Consistent with this interpretation, Moriyama and his colleagues have isolated and partially purified a growth hormone-like peptide from abalone, and this peptide also stimulates growth (Moriyama, et al., 1989, 1992).

The present invention describes recombinant vectors and methods by which genes may be introduced that affect mollusk growth. Following the method of the present invention, the abalone GH gene is cloned in, for example, the actin cassette expression vector such that the resulting protein expression product is an actin/GH fusion protein. Alternatively, the actin regulatory sequences are used to replace the GH regulatory sequences, thus placing the GH gene under the transcriptional and translational control of the actin gene regulatory sequences.

Further, the methods of the present invention may be used to modify endogenous copies of the GH gene by deleting normal GH gene regulatory sequences and replacing them with regulatory sequences conferring higher levels of expression (i.e., gene replacement).

B. Other Potentially Useful Genes

In addition to the use of abalone growth hormone gene to enhance the growth rates and ultimate sizes of transgenic abalone, the Insulin-like Growth Factor (IGF 1) gene may also be used to enhance growth via its positive regulation of GH (Sara and Hall, 1990). The IGF 1 gene has recently been isolated from oysters. IGF 1-like sequences from a variety of organisms can be used to generate degenerate primers for the isolation of the abalone homologue of the IGF 1 gene (as described herein for isolation of the abalone β-actin gene).

V. UTILITY

The present invention includes a method of transforming members of the phylum mollusca. This phylum includes the class Gastropoda, which includes abalones.

A. Vectors and Strain Variants

The present invention provides vectors suitable for the transformation of mollusks. Such vectors can be sold individually or in kits for use in the transfection and transformation methods of the present invention. Kits may also include buffers useful for transformation.

The vectors and methods of the present invention can be used to generate transgenic aquatic organisms, such as, transgenic abalone. The vectors and methods can be used to introduce heterologous DNA or, alternatively, to modify endogenous genes by recombinant genetic methods. Such transgenic organisms may be manipulated to have enhanced growth rates as described above. In addition to increased growth, strains may be engineered that have other properties such as disease resistance, shell and/or meat coloration, meat texture, and taste. This technology can be extended to other commercially important mollusks as well as abalone.

B. Genetic Analysis

The transfection method of the present invention complements more classical genetic approaches. The efficiency of gene expression described herein makes possible detailed studies on the expression of genes important to the processes of growth and organismal development. Further, the transformed organisms of the present invention provide means for screening compounds (typically by employing the effects of such compounds on the expression of reporter genes, e.g., a reporter gene under the control of the GH promoter) effective to interfere with or promote such processes. The transgenic mollusks of the present invention are also vehicles for the expression of heterologous proteins encoded by DNA introduced by transfection.

The vectors and methods of the present invention also provide the means for recombinant genetic manipulations of mollusks, including gene replacements and gene knockouts.

While preferred embodiments, uses, and methods of practicing the present invention have been described in detail, it will be appreciated that various other uses, formulations, and methods of practice as indicated herein are within the contemplation of the present invention.

MATERIALS AND METHODS

*E. coli* DNA polymerase I (Klenow fragment) was obtained from Boehringer Mannheim Biochemicals (BMB) (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio, et al.; Eaton, et al.). Oligonucleotide coding sequences can be expressed by standard recombinant procedures (Maniatis, et al.; Ausubel, et al.).

Standard molecular biology and cloning techniques were performed essentially as previously described in Ausubel, et al., Sambrook, et al., and Maniatis, et al.

Polymerase chain reactions were carried out essentially per the manufacturer's instructions. Polymerase chain reaction methods are generally described in Kawasaki, Mullis, and Mullis, et al.

Fertilized eggs were obtained from Pacific Mariculture Inc., 5515 Coast Road, Santa Cruz, Calif. 95060. Other sources for fertilized eggs are as follows: The Abalone Farm Inc., P.O. Box 136, Cayocos, Calif. 93430; and Ab Lab, 560 Center Drive, Port Hueneme, Calif. 93043-4328.

EXAMPLE 1

Construction of Plasmids

Figure 7:
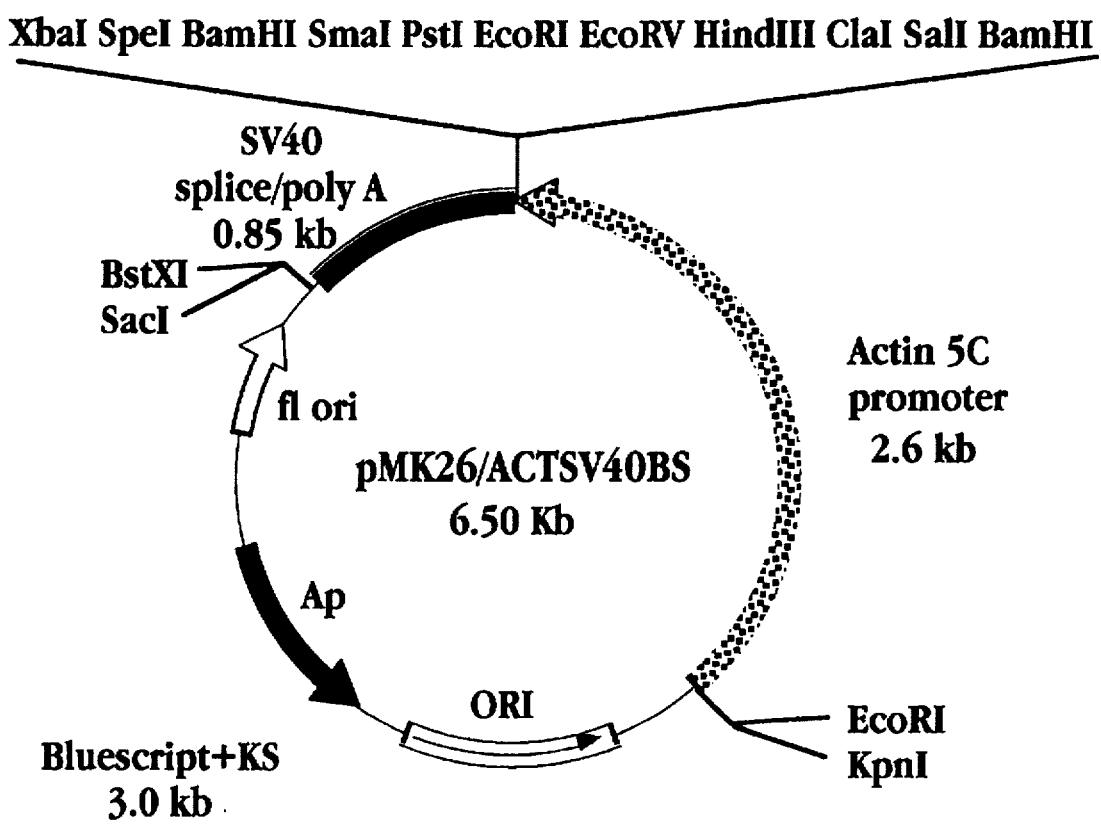
FIG. 7 presents a schematic map of vector pMK26 containing the *Drosophila melanogaster* ACT 5C promoter.

The plasmids pMK18 and pLH2 were constructed from pMK26 (FIG. 7; Koelle, et al., 1991, pMK26=pAct/SV40/BS). Plasmid pMK26 contains the *Drosophila melanogaster* ACT5-C promoter, a β-actin promoter. This promoter is expressed throughout development and in most adult tissues (Fryberg, et al., 1983). Both vectors were constructed from pMK26 modified as follows: pMK26 was partially digested with EcoRI and the EcoRI site, next to the KpnI site in pMK26 (FIG. 7), was filled in using Klenow and dNTPs (Ausubel, et al.; Maniatis, et al.). The resulting plasmid was recircularized by blunt end ligation and a modified pMK26 having a single EcoRI site was identified by restriction mapping.

pMK 18 was constructed by inserting the 4.8 β-galactosidase ubx cassette of cP bxd6.2 (Irvine, et al., 1991) by blunt end ligation of the fragment into the SmaI site of modified-pMK26. For electroporation plasmids were linearized at the unique EcoRI site.

For the construction of pLH2, a 1070 KB HindIII fragment containing the csGH gene, as well as all of the 5'-untranslated leader and 373 BP of the 3' untranslated region, were obtained from pRSVCSGH (Gonzalez-Villansenor, et al.). The HindIII fragment was ligated into the unique HindIII site in the modified pMK26 poly linker. This plasmid was linearized with EcoRI for electroporation. The DNA sequence of csGH is presented as SEQ ID NO:1. The entire translated sequence of csGH is presented as SEQ ID NO:2.

The pLUC vector was generated as follows. The 2.0 kb XhoI/StyI fragment of pXP2 (Nordeen, Biotechniques 6:454-457, 1988) was isolated which contains the luciferase gene and SV40 regulatory sequences. This fragment was cloned into XhoI/StyI digested pBLCAT6 (Boshart, et al., Gene 110:129-130, 1992) to generate a promoter-less luciferase-containing vector.

The pCMVtkLUC vector contained the luciferase gene under the control of an HSV thymidine kinase promoter with a CMV enhancer.

EXAMPLE 2

Introduction of DNA into Abalone

For introduction of DNA, 200 μl of fertilized abalone eggs, at a concentration of 4000-6000 eggs/200 μl, were added to each Baekon 2000 electroporater cuvette. Each cuvette contained 100 μl of linearized plasmid DNA, at a concentration of 2 mg/ml, and 400 μl of artificial seawater.

A typical artificial sea water is composed as follows: 24.72 g/l NaCl, 0.67 g/l KCl, 1.36 g/l $CaCl_2.2(H_2O)$, 4.66 g/l $MgCl_2.4(H_2O)$, 6.29 g/l $MgSO_4.7(H_2O)$, 0.18 g/l sodium carbonate, pH 7.8.

Electroporation conditions were as follows: 10 KV, 6 cycles, pulse time:160 uS, and burst time 1.6 seconds. Following electroporation, the eggs were put into 1 liter of sea water containing 100 μg/l each penicillin and streptomycin (pen/strep; Life Technologies, Gaithersburg, Md.). The eggs/larvae were cultured at 14° C. with aeration. The seawater/pen/strep were changed every day.

EXAMPLE 3

Genomic DNA Hybridization Analysis of Transgenic Abalone

A. DNA Uptake and Retention

Abalone eggs, transfected with the vectors described above, were evaluated for the presence of transfecting DNA. DNA was extracted from electroporated eggs two hours (first cleavage division) and twenty-four hours (trochophore larvae) post-fertilization (Hahn, 1989). The first time point monitored DNA uptake, while the second monitored DNA retention.

For each time point a pool of 5 eggs or larvae were ground in 10 μl of TE (Maniatis, et al.) in an "EPPENDORF" microcentrifuge tube using a homogenizer. Debris was cleared and the nucleic acid precipitated. Resuspended DNA samples were then transferred to nitrocellulose using a dot blot capture system (Ausubel, et al.; Schleicher and Schuell).

Exemplary results of such a dot blot analysis is presented in FIG. 1. This figure demonstrates uptake and retention of plasmid DNA into electroporated abalone eggs. The DNA bound to the nitrocellulose filters was hybridized with radiolabelled plasmid pMK18 DNA (random primer, Boehringer-Mannheim, Indianapolis Ind.). In FIG. 1, the first two slots from the left, in the bottom row of the two hour samples, are DNA extracted from non-electroporated eggs. The standards are presented in the top panel of the figure, from left to right, 600, 300, 100, 60 and 30 picograms of pMK18 DNA.

The data obtained in this manner suggested that DNA is taken up and retained in approximately 80-100% of all electroporated eggs.

B. Retention of Transfected DNA

Abalone transfected with the pMK18 vector were grown. DNA was extracted from three-month-old juveniles and analyzed by dot blots using radiolabelled plasmid pMK18 DNA. FIG. 2 shows the dot blot hybridization data for the transgenic abalone and un-transformed controls. Concentration standards are (from left to right) 600, 400, 100, 60, 30, 10, 6 and 3 picograms of pMK18 DNA.

The results in FIG. 2 demonstrate the retention of electroporated DNA in three-month-old juvenile abalone.

C. DNA Hybridization Analysis of 3-Month Old Juvenile Transgenic Abalone

The DNA samples isolated from 3 month old juvenile transgenic abalone (above) were loaded onto agarose gels, size fractionated and transferred to nitrocellulose filters (Ausubel, et al.; Sambrook, et al.). The filters were hybridized with radioactively labeled pMK18. Autoradiograms of these filters demonstrated that the pMK18 homologous sequences were present in high molecular weight DNA. The results are presented in FIG. 3B. In the figure, the DNA samples in the two lanes were isolated from two different animals. The DNA in the left hand panel is integrated. The DNA in the right hand panel has not integrated.

To distinguish between concatemers and integration of pMK18, the genomic DNA samples were digested with the restriction endonuclease HindIII. This restriction endonuclease cuts asymmetrically in the EcoRI linearized plasmid that was used for electroporation (see FIG. 3A). The DNA on the nitrocellulose filters was hybridized with a 200 bp polymerase chain reaction (Perkin-Elmer/Cetus, Norwalk, Conn.) amplified fragment from an 8 kb HindIII/EcoRI fragment of pMK18 (see FIG. 3A).

A strong 8 kb signal was observed that corresponded to two of the three possible types of concatenates (FIG. 3B). The 8 kb signal was observed in all genomic DNA samples indicating the presence of concatenates in each sample.

An approximately 16 kb signal was also observed in some of the DNA samples. The 16 kb signal corresponded to the third type of concatenate (FIG. 3A). These results suggest that most of the concatenates may be head-to-tail multimers.

Junction fragments were observed in approximately 70% of the DNA samples derived from transgenic abalone (FIG. 3B, e.g., signals appearing at molecular weights of less than 8 kb). This result suggests an extremely high degree of integration.

EXAMPLE 4

Analysis of Gene Expression in Transgenic Abalone

The vector pMK18 contained an expression cassette for β-galactosidase. Transgenic abalone bearing the vector were assayed for the expression of β-galactosidase over time.

Pools of fifty larvae were extracted at various intervals during the period of larval development and the levels of β-galactosidase determined using the fluorescent substrate 4-methylumbelliferyl-β-D-galactoside (Sigma Chemical Co., St. Louis, Mo.) essentially as previously described by Koelle, et al. (1991).

FIG. 4 presents the data from exemplary fluorescence experiments for the expression of β-galactosidase in electroporated larvae. Fluorescence units are on the Y-axis and time in days (post fertilization) is presented of the X-axis. Enzyme activity is expressed in arbitrary fluorescence units.

The data presented in FIG. 4 are the average 5 separate electroporation experiments for plasmids pMK18 and two separate experiments for control plasmid CMVLac. CMVlac is a vector carrying the cytomegalovirus promoter adjacent the β-galactosidase gene (e.g., "pCMVβ" Clontech, Palo Alto Calif.). The standard errors have not been computed; however, the variation among experiments was less than 5%.

The data suggest that β-galactosidase is expressed when pMK18 (β-actin promoter) was employed. The decline in enzyme activity is not due to loss of plasmid sequences, since dot blots reveal the retention of plasmid DNA throughout the larval period.

The vertebrate retroviral promoter CMV does not seem to be active in transgenic abalone. Similar results were obtained with the RSV promoter.

EXAMPLE 5

Identification and Isolation of Abalone Actin Gene and Construction of Mollusk Expression Vectors

Figure 5A:
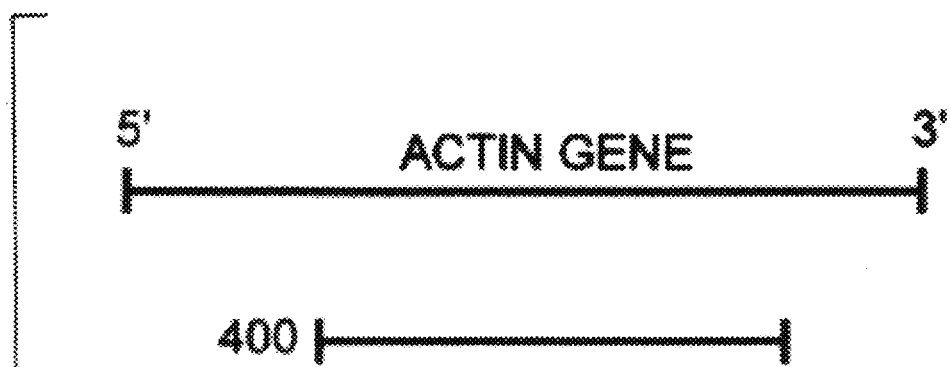
FIG. 5A shows a schematic of an actin gene and an internal 400 bp region.

A. Isolation of an Approximately 400 Base Pair Fragment of the Abalone Actin Gene A set of degenerate primers for invertebrate actin (based on the "GENBANK" sequences for *D. Melanogaster* (5CX, 8F, 87E), *B. Moryi* (A1, A2, A3) actin genes) was designed. The sequences of these primers are presented as SEQ ID NO:3 and SEQ ID NO:4. These primers amplify an approximately 400 bp fragment within the target coding regions (FIG. 5A). A schematic of the isolation of this approximately 400 bp fragment is presented in FIG. 8A.

RNA was isolated from abalone ovary tissue (R. A. Cox I Methods in Enzymology, L. Grossman and K. Moldave, Eds., Vol 12, partB. pp. 120–129, Academic press, Orlando, Fla., (1988); "RNAZOL" kit from Tel-Test, Inc. Friendswood, Tex.).

cDNA was synthesized from 5 µg of total ovary RNA, in a final volume of 20 µl, using 10 ul of reverse transcriptase (Invitrogen, San Diego, Calif.). One µl of each cDNA sample was used in a 100 µl polymerase chain reaction (PCR) including the primers at 20 µM. Polymerase chain reaction conditions and protocols were generally similar to those found in commercially available kits (Perkin-Elmer, Norwalk, Conn.).

Amplified products were resolved on the basis of size using electrophoresis. After amplification, approximately 7% of each reaction product mixture was separated by electrophoresis in 1% agarose gels (FMC Bioproducts, Rockport, Me.). Gels were stained with ethidium bromide for visualization under UV illumination.

Figure 5B:
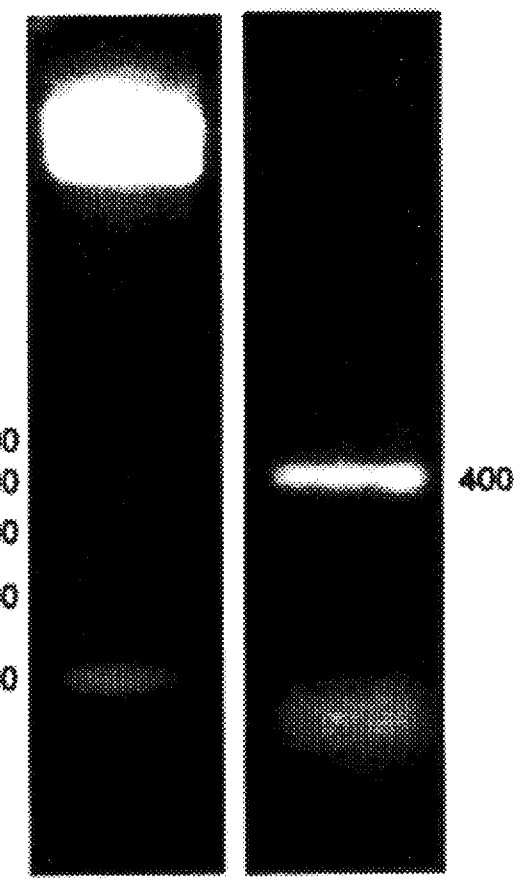
FIG. 5B shows PCR amplification of actin-specific sequences.

The results of one such analysis are presented in FIG. 5B. The first lane of the figure shows the amplification products resulting from amplification utilizing the degenerate actin primer set and DNA from ovary. The second lane shows the amplification products resulting from amplification utilizing the degenerate actin primer set and total abalone ovary RNA. The expected amplification product of approximately 400 bp was observed in the second lane.

The sequence of this 400 bp fragment was confirmed by standard DNA sequencing methods.

B. Isolation of the Abalone Actin Promoter Sequences

Abalone actin gene sequence specific primers were derived from the approximately 400 base pair sequence described above. A primer was selected to be complementary to the DNA strand corresponding to the actin protein coding sequence (FIG. 8B).

An abalone genomic DNA library was generated in lambda gt 10 (Ausubel, et al.; Stratagene). This library was employed as the DNA substrate in polymerase chain reaction amplifications using the actin specific primer just described as the first primer and a set of random primers (BMB, Indianapolis, Ind.) as the second primer (FIG. 8B).

Genomic walking experiments lead to the isolation of the genomic coding sequences of the abalone actin gene. FIG. 9 (SEQ ID NO:5) presents a partial sequence of 1540 base pairs representing a 5' coding region of the actin gene and accompanying 5' non-coding sequences. Sequencing and RNase protection assays were performed in order to map the gene's intron positions and the transcription start point. The structure of the abalone gene corresponding to the sequence presented in FIG. 9 is diagrammatically represented in FIG. 10. Promoter motifs (e.g., the TATA box) and the promoter region are illustrated in the figure, as are two exons and an intron of the actin protein coding region.

Figure 11:
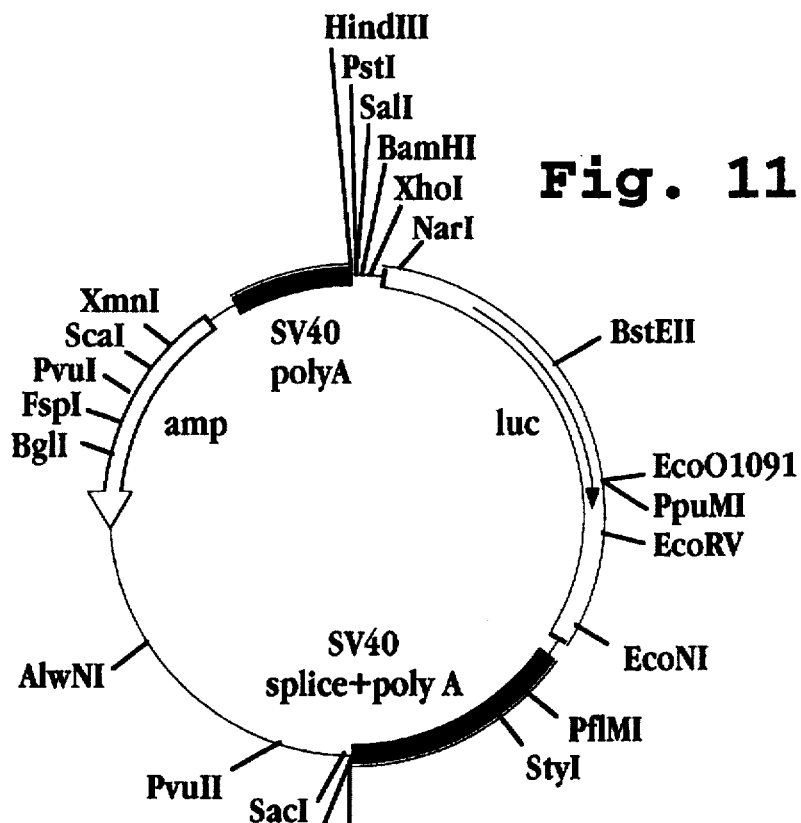
FIG. 11 presents a schematic map of vector pLUC containing the luciferase reporter gene.
Figure 12:
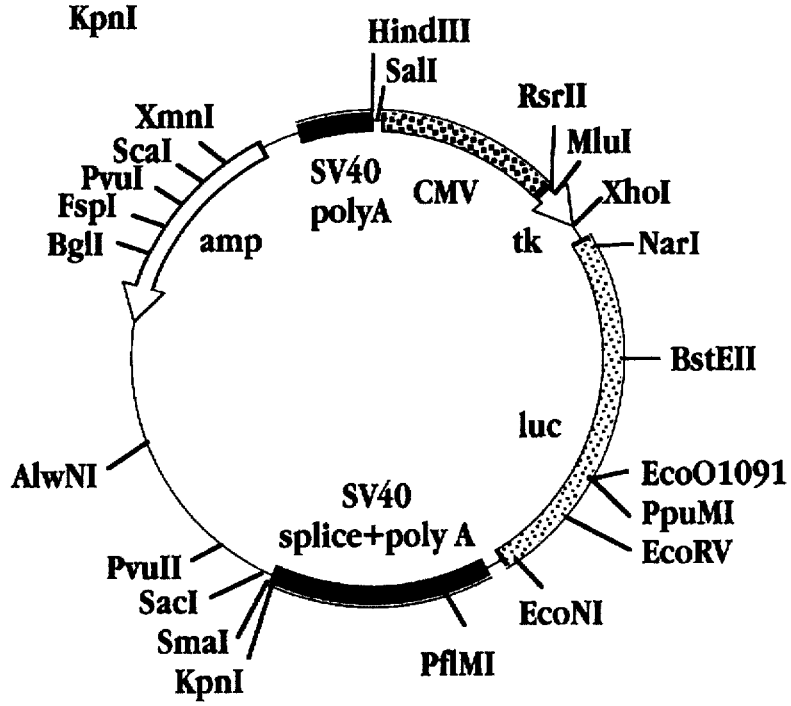
FIG. 12 presents a schematic map of vector pCMVtkLUC, a control plasmid containing the luciferase reporter gene.

The two expression vector constructs were created with the actin sequences. First, essentially the entire clone was introduced into the multiple cloning site of the vector pLUC (FIG. 11). This vector was designated pABA1600LUC. A second vector was created having approximately the first 800 bp of SEQ ID NO:5 introduced into the multiple cloning site of pLUC (designated pABA800LUC). The reporter gene in these vector constructs was the luciferase gene (LUC).

pABA1600LUC, pABA800LUC, pLUC (negative control, Example 1) and pCMVtkLUC (positive control, Example 1) were transfected into Human Embryonic Kidney Cell Line ATK293 following standard calcium phosphate transfection procedures.

Transient expression assays using these transformed cell lines were performed. The activity of the abalone actin promoter in the transfection assays was determined as fg Luciferase per U galactosidase. Percent activity was determined relative to the negative control (cells transformed with pLUC alone). The results of this analysis are presented in Table 2.

TABLE 2

|  | fg Luciferase/ U galactosidase | % Activity |
| --- | --- | --- |
| pLUC | 7 | — |
| pCMVtkLUC | 382 | 311 |
| pABA1600LUC | 47 | 38 |
| pABA800LUC | 123 | 100 |

These results demonstrate the ability of the cloned actin sequences to provide promoter function in expression vector constructs.

C. Generation of Abalone Actin Promoter-Based Vectors

For ease of manipulation, the β-actin sequences are cloned into a shuttle vector. For example, the "SK+ BLUE-SCRIPT" vector provided sequences allowing the replication and selection of the vector constructs in a bacterial host. Other known bacterial vector systems (e.g., Clontech, Palo Alto, Calif.) can be used in this capacity as well. Further, yeast vectors can be used in the practice of the present invention (e.g., Hitzeman, et al.; Rutter, et al.; Oeda, et al.). The yeast transformation host is typically *Saccharomyces cerevisiae*, however, other yeast suitable for transformation can be used as well (e.g., *Schizosaccharomyces pombe*).

For generating vectors for the expression of heterologous DNA (DNA not originally derived from the organism being transformed), transcriptional and translational regulatory sequences (including initiation and termination sequences) are typically obtained from 5' and 3' non-coding regions of genes (as described above for β-actin from abalone).

To further characterize specific active promoter sequences, the 5' non-coding sequences, containing actin gene promoter sequences identified by sequence comparisons (FIG. 10), and contiguous 5' coding sequences are fused in-frame to reporter protein coding sequences, such as β-galactosidase, luciferase or chloramphenicol acetyltransferase (CAT) (Gorman).

A series of plasmids, containing the β-actin 5'-end and reporter gene, are constructed by Exo III digestion of the 5' distal end of the promoter containing region (Hoheisel and Pohl, 1986; Henikoff, 1987). The deletion series is transfected into abalone eggs as described above and the eggs assayed for the expression of the reporter gene. Plasmids expressing the reporter gene are sequenced to determine the endpoints of the deletions.

Appropriate expression plasmids are constructed containing various proportions of the actin promoter and the 5' and 3' untranslated regions. Unique restriction sites will be inserted between the 5' and 3' untranslated regions for rapid cloning. DNA uptake and integration using this vector is determined by dot blots and DNA hybridization assays, as described above.

While the invention has been described with reference to specific methods and embodiments, it will be appreciated that various modifications and changes may be made without departing from the invention.

It is claimed:

1. A transgenic abalone containing a DNA sequence heterologous to said abalone, wherein
   (i) said DNA sequence is flanked by regulatory sequences causing expression in said abalone of said DNA sequence, and
   (ii) said DNA sequence expresses a polypeptide that promotes growth enhancement of the transgenic abalone relative to wild-type abalone.

2. A transgenic abalone of claim 1, where said regulatory sequences are derived from an actin gene.

3. A transgenic abalone of claim 1, where said regulatory sequences are derived from abalone.

4. A transgenic abalone of claim 3, where said regulatory sequences include a promoter derived from an abalone actin gene.

5. A transgenic abalone of claim 4, where said promoter sequence is derived from SEQ ID NO:5.

6. A transgenic abalone of claim 1, where said DNA sequence is flanked by regulatory sequences derived from a *Drosophila melanogaster* gene.

7. A transgenic abalone of claim 6, where said regulatory sequences are derived from the ACT-5 promoter.

8. A transgenic abalone of claim 1, where said heterologous DNA sequence encodes a growth factor.

9. A transgenic abalone of claim 8, where said growth hormone is coho salmon growth factor.

10. A transgenic abalone containing a DNA sequence heterologous to said abalone, wherein
    (i) said DNA sequence is flanked by regulatory sequences causing expression in said abalone of said DNA sequence, and
    (ii) said DNA sequence expresses a marker polypeptide.

11. An expression vector useful for transformation of an abalone comprising
    a first DNA sequence flanked by regulatory elements effective to allow expression of the sequence in said abalone, wherein said regulatory elements are derived from an abalone actin gene, and
    second DNA sequences allowing the propagation of the vector in a secondary host,
    wherein said regulatory elements include a promoter sequence derived from SEQ ID NO:5.

12. An expression vector of claim 11, where said second DNA sequences include an origin of replication and a selectable marker.

13. An expression vector of claim 11, where said secondary host is bacterial.

14. An expression vector of claim 11, where said first DNA sequence encodes a growth hormone.

15. An expression vector of claim 14, where said growth hormone is coho salmon growth hormone.

16. A method for transfecting an abalone, comprising,
    introducing an expression vector by electroporation into a fertilized abalone egg, said vector containing a DNA sequence flanked by regulatory elements effective to allow expression of the sequence in abalone,
    culturing said abalone egg under conditions that allow development of the egg into an abalone, and
    identifying a transfected abalone based on the presence of said DNA sequence.

17. A method of claim 14, where said transfecting includes integration of the vector at a genomic site.

18. A method of claim 16, where said DNA sequence encodes a growth hormone.

19. A method for enhancing the weight of an abalone relative to a wild-type abalone, comprising introducing a vector by electroporation into a fertilized abalone egg, said vector containing a DNA sequence flanked by regulatory elements effective to allow expression of the sequence in abalone, where said DNA sequence encodes a gene product that promotes growth enhancement and said DNA sequence and regulatory elements become integrated into the abalone egg genome, culturing said abalone egg under conditions that allow development of the egg into a transgenic abalone, and growing said transgenic abalone under conditions causing expression of the gene product, wherein the weight of the transgenic abalone is enhanced relative to the weight of a wild-type abalone.

20. A method of claim 19, where the gene product that promotes growth enhancement is a growth hormone.

21. A duplex DNA fragment containing a DNA sequence encoding a polypeptide, adjacent said DNA sequence a promoter effective to promote transcription of said DNA sequence, where said promoter is an abalone actin gene promoter derived from SEQ ID NO:5 and said DNA sequence is heterologous to the abalone actin gene promoter.

22. A duplex DNA fragment of claim 21, where the polypeptide is a growth hormone.

23. A duplex DNA fragment of claim 22, where said growth hormone is coho salmon growth hormone.

24. A method for expressing a protein in an abalone, comprising introducing an expression vector by electroporation into a fertilized abalone egg, said vector containing a DNA sequence flanked by regulatory elements effective to allow expression of the sequence in abalone and said DNA sequence and regulatory elements becoming integrated into the abalone egg genome, culturing said abalone egg under conditions that allow development of the egg into an abalone, and growing the abalone under conditions permissive for the expression of the protein, wherein said growing results in expression of the protein.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1201 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO (  v  i  ) ORIGINAL SOURCE:
    (  C  ) INDIVIDUAL ISOLATE: Coho Salmon Growth Hormone Gene (  i  x  ) FEATURE:
    (  A  ) NAME/KEY: CDS
    (  B  ) LOCATION: 65..697
    (  D  ) OTHER INFORMATION: /note="Growth Hormone Precursor"

(  i  x  ) FEATURE:
    (  A  ) NAME/KEY: sig_peptide
    (  B  ) LOCATION: 65..130
    (  D  ) OTHER INFORMATION: /note="growth hormone signal
              peptide"

(  i  x  ) FEATURE:
    (  A  ) NAME/KEY: mat_peptide
    (  B  ) LOCATION: 131..697
    (  D  ) OTHER INFORMATION: /note="Growth Hormone"

(  x  i  ) SEQUENCE DESCRIPTION: SEQ ID NO:1:

| | | | | | |
|---|---|---|---|---|---|
| TACATACTCA | ACCGACCACC | GCACTTTCAA | GTTAAGTAAC | CATCCTTGGC | AATTAAGAGT | 60 |
| AAAAATGGGA | CAAGTGTTTC | TGCTGATGCC | AGTCTTACTG | GTCAGTTGTT | TCCTGAGTCA | 120 |
| AGGGGCAGCG | ATAGAAAACC | AACGGCTCTT | CAACATCGCG | GTCAGTCGGG | TGCAACATCT | 180 |
| CCACCTATTG | GCTCAGAAAA | TGTTCAATGA | CTTTGACGGT | ACCCTGTTGC | CTGATGAACG | 240 |
| CAGACAGCTG | AACAAGATAT | TCCTGCTGGA | CTTCTGTAAC | TCTGACTCCA | TCGTGAGCCC | 300 |
| AGTCGACAAG | CACGAGACTC | AGAAGAGTTC | AGTCCTGAAG | CTGCTCCATA | TTTCTTTCCG | 360 |
| TCTGATTGAA | TCCTGGGAGT | ACCCTAGCCA | GACCCTGATC | ATCTCCAACA | GCCTATTGGT | 420 |
| CGGAAACGCC | AACCAGATCT | CTGAGAAGCT | CAGCGACCTC | AAAGTGGGCA | TCAACCTGCT | 480 |
| CATCATGGGG | AGCCAGGATG | GCCTACTGAG | CCTGGATGAC | AATGACTCTC | AGCAGCTGCC | 540 |
| CCGCTACGGG | AACTACTACC | AGAACCCGGG | GGGCGACGGA | AACGTCAGGA | GGAACTACGA | 600 |
| GTTGTTGGCT | TGCTTCAAGA | AGGACATGCA | CAAGGTCGAG | ACCTACCTGA | CCGTCGCCAA | 660 |
| GTGCAGGAAG | TCACTGGAGG | CCAACTGCAC | TCTGTAGACG | TGGGCTGGAG | AGGCAGCCAG | 720 |
| CAAGAGCCTG | TCTCCAGGGT | TTGGTTTCCC | AGATACAGAT | TAGGCCTTGC | CCTGCACTGA | 780 |
| GGTGCATTTT | CAATTGAGAT | TCTCCATTGA | ACATGCTTTT | CAGTCTAGAG | TAATTTCATT | 840 |
| TTGGATCTGG | TAGAGCCTGA | CTCCAGGGGT | TTTCAGGCAT | TTGCACTTTT | TTTCTCTGAA | 900 |
| ATCAACAACA | ACACTTTCTA | TATTGACTCT | ATCACTCTGA | GCTACCATTG | ATTAGTACAT | 960 |
| TTATAGAAAA | GGTTATTAAA | TGTCTTATTT | AGATATATGG | TTCATGGCGG | TGCTACTGTT | 1020 |
| TATGCATACG | TTAATATTTA | GGGGTGAAAT | GGGAACTTGT | AGAGCTCCAA | GCTTTTGGAT | 1080 |
| AATATATTTT | AGAGTAATTT | CCTTTAAGTA | TTTTCATTCC | TTAATCTTAT | TGTTTGAAAC | 1140 |
| TAATAGTGAT | TCATGTTTCA | ATAAAGATGT | TCTTCTCTGC | AGCAAAAAAA | AAAAAAAAA | 1200 |
| A | | | | | | 1201 |

(  2  ) INFORMATION FOR SEQ ID NO:2:

(  i  ) SEQUENCE CHARACTERISTICS:
    (  A  ) LENGTH: 210 amino acids
    (  B  ) TYPE: amino acid
    (  D  ) TOPOLOGY: linear (  i  i  ) MOLECULE TYPE: protein (  i  i  i  ) HYPOTHETICAL: NO (  i  v  ) ANTI-SENSE: NO (  v  i  ) ORIGINAL SOURCE:
    (  C  ) INDIVIDUAL ISOLATE: Coho Salmon Growth Hormone ( x i ) SEQUENCE DESCRIPTION: SEQ ID NO:2:

```
Met Gly Gln Val Phe Leu Leu Met Pro Val Leu Leu Val Ser Cys Phe
1               5                   10                  15

Leu Ser Gln Gly Ala Ala Ile Glu Asn Gln Arg Leu Phe Asn Ile Ala
            20                  25                  30

Val Ser Arg Val Gln His Leu His Leu Leu Ala Gln Lys Met Phe Asn
        35              40                  45

Asp Phe Asp Gly Thr Leu Leu Pro Asp Glu Arg Arg Gln Leu Asn Lys
    50                  55                  60

Ile Phe Leu Leu Asp Phe Cys Asn Ser Asp Ser Ile Val Ser Pro Val
65              70                  75                      80

Asp Lys His Glu Thr Gln Lys Ser Ser Val Leu Lys Leu Leu His Ile
                85                  90                      95

Ser Phe Arg Leu Ile Glu Ser Trp Glu Tyr Pro Ser Gln Thr Leu Ile
            100             105                 110

Ile Ser Asn Ser Leu Leu Val Gly Asn Ala Asn Gln Ile Ser Glu Lys
        115                 120                 125

Leu Ser Asp Leu Lys Val Gly Ile Asn Leu Leu Ile Met Gly Ser Gln
    130                 135                 140

Asp Gly Leu Leu Ser Leu Asp Asp Asn Asp Ser Gln Gln Leu Pro Arg
145                 150                 155                 160

Tyr Gly Asn Tyr Tyr Gln Asn Pro Gly Gly Asp Gly Asn Val Arg Arg
                165                 170                 175

Asn Tyr Glu Leu Leu Ala Cys Phe Lys Lys Asp Met His Lys Val Glu
            180                 185                 190

Thr Tyr Leu Thr Val Ala Lys Cys Arg Lys Ser Leu Glu Ala Asn Cys
        195                 200                 205

Thr Leu
210
```

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Actin 5' Primer ( i x ) FEATURE:
        ( A ) NAME/KEY: misc_feature
        ( B ) LOCATION: 12
        ( D ) OTHER INFORMATION: /note="Where N is C or T"

( i x ) FEATURE:
        ( A ) NAME/KEY: misc_feature
        ( B ) LOCATION: 24
        ( D ) OTHER INFORMATION: /note="Where N is C or T"

( i x ) FEATURE:
        ( A ) NAME/KEY: misc_feature
        ( B ) LOCATION: 27
        ( D ) OTHER INFORMATION: /note="Where N is G or A"

( x i ) SEQUENCE DESCRIPTION: SEQ ID NO:3:

GAGAAGATGA CNCAGATCAT GTTNGANAC      29

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Actin 3' Primer ( i x ) FEATURE:
        ( A ) NAME/KEY: misc_feature
        ( B ) LOCATION: 4
        ( D ) OTHER INFORMATION: /note="Where N is G or Inosine"

( i x ) FEATURE:
        ( A ) NAME/KEY: misc_feature
        ( B ) LOCATION: 7
        ( D ) OTHER INFORMATION: /note="Where N is C or G"

( i x ) FEATURE:
        ( A ) NAME/KEY: misc_feature
        ( B ) LOCATION: 16
        ( D ) OTHER INFORMATION: /note="Where N is G or Inosine"

( i x ) FEATURE:
        ( A ) NAME/KEY: misc_feature
        ( B ) LOCATION: 17
        ( D ) OTHER INFORMATION: /note="Where N is G or A"

( i x ) FEATURE:
        ( A ) NAME/KEY: misc_feature
        ( B ) LOCATION: 18
        ( D ) OTHER INFORMATION: /note="Where N is T or C"

( x i ) SEQUENCE DESCRIPTION: SEQ ID NO:4:

```
CATNATNGAG TTGTANNNGG TCTCGTGGAT                                    30
```

( 2 ) INFORMATION FOR SEQ ID NO:5:

( i ) SEQUENCE CHARACTERISTICS:
        ( A ) LENGTH: 1540 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: ABALONE ACTIN GENE SEQUENCE ( x i ) SEQUENCE DESCRIPTION: SEQ ID NO:5:

```
GGAACAGTGT  CAAACATATA  TACAAGCTTG  ATGGTGAGAA  ATATTAGCAT  TAATACTGTC    60
ACTTGTTGTT  TAGCATATTA  TTTCTGATAT  ATAAATACTT  AGGAAATTCT  ATTTTTCTCA   120
TGCAAAAAGC  CACTTAACTT  CATCAATAAA  ATCGTTATCT  GCACCTAAGA  ATGATCTTCC   180
ATCATCTCTA  TGTTGACATA  CGTTTTATCA  TCCAGATTAT  CAATGAAAGT  CGAAAAGATT   240
ACAACTCCCT  CTGAAATATG  AATATTCACA  GTTTAGAGGG  CAAGTAAAGC  CAACACAACT   300
ACTTTGCACG  GCGAGAACAA  GCAATATCAG  GGTGTTACAT  TCTGTACATT  CGTTAGATAT   360
```

-continued

| | | | | | |
|---|---|---|---|---|---|
| TTTACTTCTG | GGTCCAATCC | TTATTACACA | CTGCATTTCT | TCCAGGAAGT | TTGGATATAA | 420 |
| CTTTACAATG | CTTTATAACT | GATGAGTAGT | AAGCGTTGTA | TGGATTTTAG | AATCTATGCA | 480 |
| TTTCCCAATA | ATGCTGATAT | ATTCATTTAA | CTTAATTTAT | TACCAGCATC | ACATTCTTGC | 540 |
| ATTCATGCTC | GTCAGCTCGA | GAAGCGCTTC | CCCATTCTCC | GCGCACCATA | CCACGTGGCG | 600 |
| TTGTCCTTGC | TTCGGGAACG | GGGGTAGGGG | GTACTTACTT | CTAGGGGAAA | GAGAGATCAG | 660 |
| TGCAGATCAC | CCCCGACTGT | GACACATTCT | TCCACATGTA | CACATGAAAG | GTTGTTATGC | 720 |
| AATATAATAC | ATTAGAAGGG | TATATTTATT | ACAATTACAA | TGGTTACGTT | TCTATTATTC | 780 |
| TCAAACACAA | TCTGATTGGT | CGCCTACTAA | TGGGGTATGT | ATAAAAGACG | CCTGGGTCAG | 840 |
| AACATCGATA | TTGCATCCGC | TTTCAGTCTT | CAGCTGACAC | ATCGTCTTTC | CCGTTCTCA | 900 |
| CACAGCAACC | TACAACCATG | GATGATGATG | TTGCTGCATT | GGTCTGTGAC | AACGGCTCCG | 960 |
| GCATGTGCAA | GGCCGGTTTT | GCCGGTGACG | ACGCTCCCAG | AGCTGTCTTC | CCCTCCATCG | 1020 |
| TCGGCCGTCC | TAGACATCAG | GTAACACCGT | TTATTGTCAC | CATGGTAACA | TAGAGGTTCA | 1080 |
| AGACCTGAAA | TATTTAGTTT | CGCCTACATT | TCGTCTCTGT | AGAATACACG | ACGTCGTACA | 1140 |
| TAATGACAAA | TGATTTCTTG | TTTCAGGGTG | TGATGGTTGG | TATGGGTCAG | AAAGACAGCT | 1200 |
| ACGTCGGTGA | CGAGGCTCAG | TCCAAGAGAG | GTATCCTCAC | TCTCAAGTAT | CCCATCGAGC | 1260 |
| ACGGTATCGC | CACCAACTGG | GACGACATGG | AGAAGATCCG | GCATCACACC | TTCTACAACG | 1320 |
| AACTCCGAGT | GGCTCCAGAG | GAGCACCYTG | TCCTYCTGAC | AGAGGCTCCC | CTCAACCCCA | 1380 |
| AGGCCAACCG | TGAAAAGATG | ACCCAGATCA | TGTTCGAGAC | CTTCAACTCT | CCAGCTATGT | 1440 |
| GTGTGGCCAT | CCAGGCTGTT | CTGTCTCTGT | ACGCTTCTGG | TCGTACCACG | GGTATTGTTC | 1500 |
| TGGACTCTGG | TGATGGTGTT | ACCCACACTG | TTCCCATCTA | | | 1540 |